United States Patent
Wood

[11] Patent Number: 5,269,405
[45] Date of Patent: Dec. 14, 1993

[54] CONTAINER OF BODY PROTECTING GARMENTS

[76] Inventor: Frederick F. Wood, 3110 Devon Ave., Medford, N.Y. 11763

[21] Appl. No.: 991,878

[22] Filed: Dec. 16, 1992

[51] Int. Cl.$^5$ ............... B65D 85/08; B65D 85/14; B65D 85/18
[52] U.S. Cl. ............... 206/69; 206/524.8; 206/278; 206/281; 206/813; 223/111
[58] Field of Search ............... 206/278, 69, 524.8

[56] References Cited
U.S. PATENT DOCUMENTS

| | | |
|---|---|---|
| 3,067,001 | 12/1962 | McCollum . |
| 3,695,493 | 10/1972 | Karr ............... 223/111 |
| 4,002,276 | 1/1977 | Poncy et al. ............... 223/111 |
| 4,069,913 | 1/1978 | Harrigan ............... 206/278 |
| 4,155,494 | 5/1979 | Poncy et al. ............... 206/278 X |
| 4,840,187 | 6/1989 | Brazier ............... 206/69 X |
| 4,915,272 | 4/1990 | Vlock ............... 223/111 |
| 5,058,785 | 10/1991 | Rich et al. ............... 223/111 |
| 5,078,308 | 1/1992 | Sullivan ............... 223/111 |
| 5,205,298 | 4/1992 | Hurst ............... 206/69 X |

*Primary Examiner*—William I. Price
*Attorney, Agent, or Firm*—Terry M. Gernstein

[57] ABSTRACT

A container stores a plurality of body protecting garments, such as surgical gloves, in a configuration that permits a user to easily don those garments. The garments are stored in layered condition, and the container has a vacuum applied thereto between the garments and the inner surface of the container, and a seal seals the garments to the container in a manner such that each garment can be removed without disturbing the vacuum. The vacuum causes the garments to inflate into a configuration that facilities donning of the garments.

20 Claims, 4 Drawing Sheets

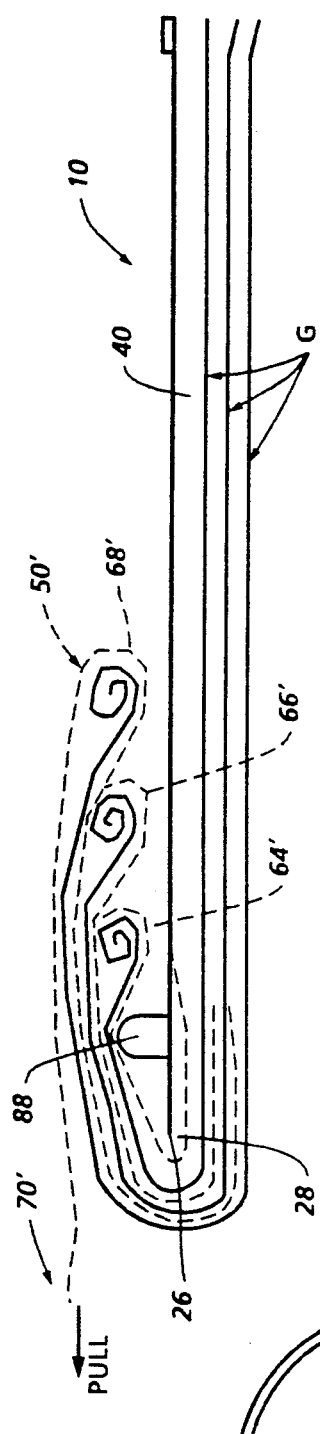
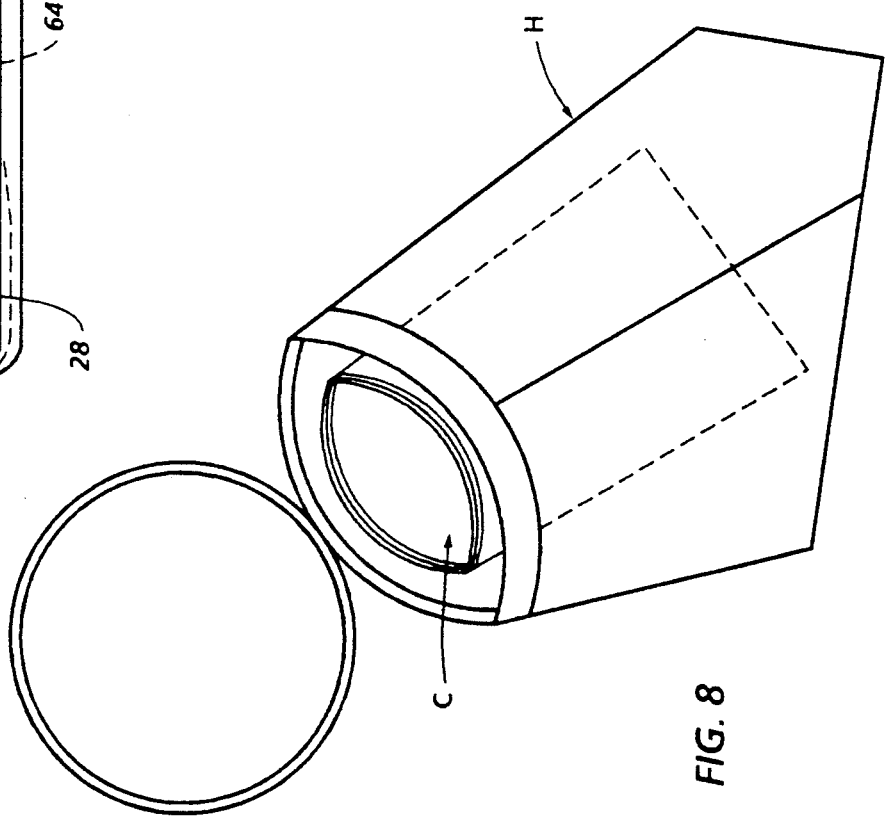

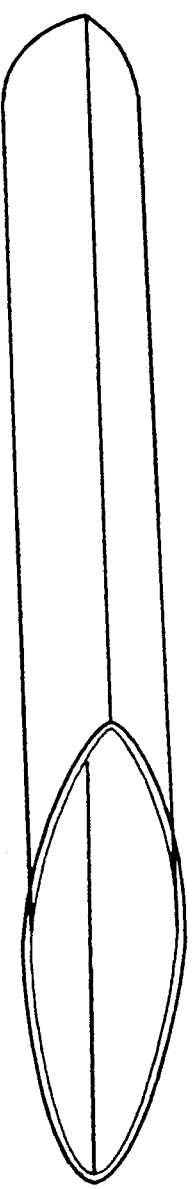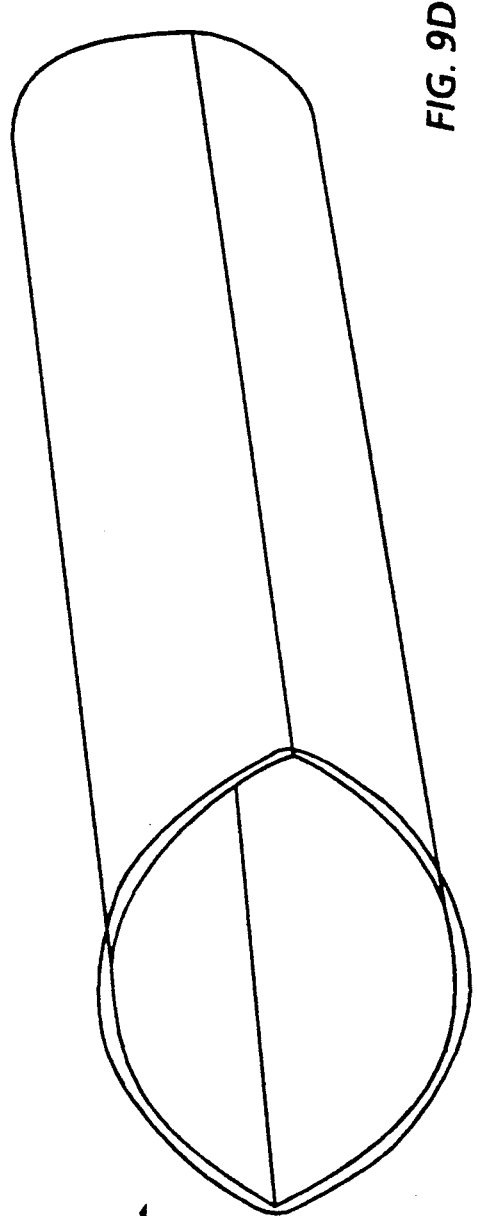
FIG. 9A
FIG. 9B
FIG. 9C
FIG. 9D

CONTAINER OF BODY PROTECTING GARMENTS

TECHNICAL FIELD OF THE INVENTION

The present invention relates to the general art of special containers, and to the particular field of containers for protective garments, such as gloves or the like.

BACKGROUND OF THE INVENTION

There are many situations in which a person needs to cover a portion of his or her body to prevent contact with another object or to prevent the spread of germs or disease. A prime example of such a situation is a health care provider, such as a surgeon, covering his or her hands with surgical gloves during a medical procedure. Such health care professionals generally change their gloves several times a day, and may (as will be discussed below) change their gloves several times during a single procedure.

Any breach in a body covering element, such as surgical gloves, used to prevent contact between a workpiece, such as a patient, and the worker, such as a health care provider, is highly undesirable, and may even be dangerous to the patient and to the health care provider. It has been found that protective garments such as surgical gloves often breach during an operation. A breach is any defect in the garment that exposes the wearer to contact, no matter how slight, with the workpiece. A breach can range from a large, visible rip in the garment to a molecule-size hole. Therefore, in order to protect both the health care provider and the patient, the health care provider should change his or her gloves often. This is especially applicable to surgeons carrying out a surgical procedure. However, it is often an onerous task to change gloves. While this may not be a problem in all situations, there are times when the time spent changing gloves is a severe intrusion on the heath care provider. At such times, the health care provider is tempted to forego changing his or her gloves. Therefore, many surgeons wear their gloves far too long during a single operation. Therefore, there is a need for a means that makes changing protective garments, such as surgical gloves, easy and expeditious for a health care provider.

Still further, if items, such as gloves, are packaged together, it may be difficult to ascertain how many items remain. This may result in a situation where the supply of items runs out and no replacement is readily available. In some situations this is not a major problem; however, in a surgical procedure where time is important, it is highly undesirable. Therefore, there is a need for a container for protective items, such as gloves, that will indicate how many items remain in the container.

In the interest of economy and environment, it is always desireable for items, such as containers, to be amenable to recycling and reuse. Therefore, it is desirable for such a container to be easily and economically manufactured.

It is noted that while the above discussion has focused on surgical gloves, the present invention is applicable to any item, including work gloves, condoms, or the like, that is used to cover a user's body, or a portion of that user's body.

Therefore, there is a need for a means for storing protective garments in a manner that facilitates their expeditious application to a user's body.

OBJECTS OF THE INVENTION

It is a main object of the present invention to provide a special container for garments used to protect a user's body.

It is another object of the present invention to provide a special container for garments used to protect a user's body that facilitates donning the garment.

It is another object of the present invention to provide a special container for garments used to protect a user's body that facilitates donning the garment and is easy to use.

It is another object of the present invention to provide a special container for garments used to protect a user's body that is inexpensive to produce.

It is another object of the present invention to provide a special container for garments used to protect a user's body that is reusable.

It is another object of the present invention to provide a special container for garments used to protect a user's body that indicates the number of garments remaining in the container.

It is a specific object of the present invention to provide a special container for surgical gloves.

It is another specific object of the present invention to provide a special container for condoms.

It is another specific object of the present invention to provide a special container for condoms that facilitates their expeditious donning.

SUMMARY OF THE INVENTION

These, and other, objects are achieved by a special container in which a plurality of protective garments, such as gloves or condoms, are stored in a manner that causes atmospheric pressure to hold the garment to be donned in position to accept the user's body portion to be protected.

Specifically, the container is adapted to store a plurality of protective garments in a layered fashion, with one garment inside another, inside an airtight container. A vacuum is applied to the container between the outermost garment and the container inner wall and the garments are sealed to each other and to the outside surface of the container wall whereby atmospheric pressure is applied to the inner surface of the innermost garment. Since the outer surface of the outermost garment is exposed to a pressure that is below atmospheric pressure, a negative pressure is applied to the garment in a manner that tends to inflate the garment towards the container wall. Such action causes the innermost garment to assume an open configuration. Since the garments are of the type that are non-breached, the seal between the outermost garment and the container wall and between each garment and its next neighbor produces an airtight seal between the container with the vacuum therein and the atmosphere. In some situations, if a garment is breached prior to its use, the negative pressure will be relieved, and the garment will deflate. Such a condition will alert a user of the breach, and that garment will not be used.

The container also includes a sealing means that seals one garment to its next outer neighbor and the outermost garment to the container wall. This seal is flexible and includes an accordion folded section in which the garments are interleaved. Each garment is releasably sealed to an accordion fold, and the sealing means is pulled away from the garment as that garment is donned. The seals between the garments and the sealing means are formed such that as one garment is removed, the vacuum is not disturbed while the next garment is exposed to atmospheric pressure. The sealing element also contains markings so that a user knows exactly how many garments remain in the container.

BRIEF DESCRIPTION OF THE DRAWING FIGURES

FIG. 7 is a partial side elevational view illustrating the view shown in FIG. 4 in larger scale and with slightly different protective garments.

FIG. 8 is a top, side and end perspective view of a housing in which a special container of the present invention is stored.

FIGS. 9A-9D are end, top and side perspective views of a container adapted for use with condoms as that container is being opened.

DETAILED DESCRIPTION OF THE PREFERRED EMBODIMENT OF THE INVENTION

Figure 1:
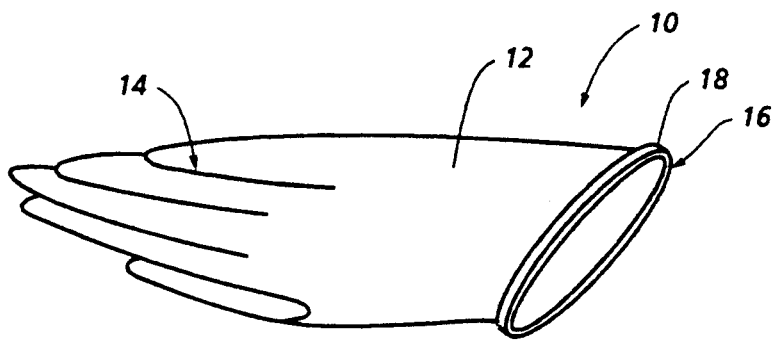
FIG. 1 is a top side and end perspective view of a surgical glove that is an example of the type of protective garments that can be stored in the special container of the present invention.

Shown in FIG. 1 is an example of a protective garment of the type that is of interest to the present disclosure. By way of example, this protective garment is a surgical glove 10, but as will occur to those skilled in the art, any other type of garment can be used without departing from the scope of the present disclosure. Glove 10 includes a body 12 having a first end 14 into which a user's fingers are placed, and a second end 16 having a cuff portion 18 thereon. The cuff portion can be unrolled when the glove is placed on a user's hand. The glove is flexible and integral. Preferably, the glove is free of any sort of breach and is thus air-impermeable.

Figure 2:
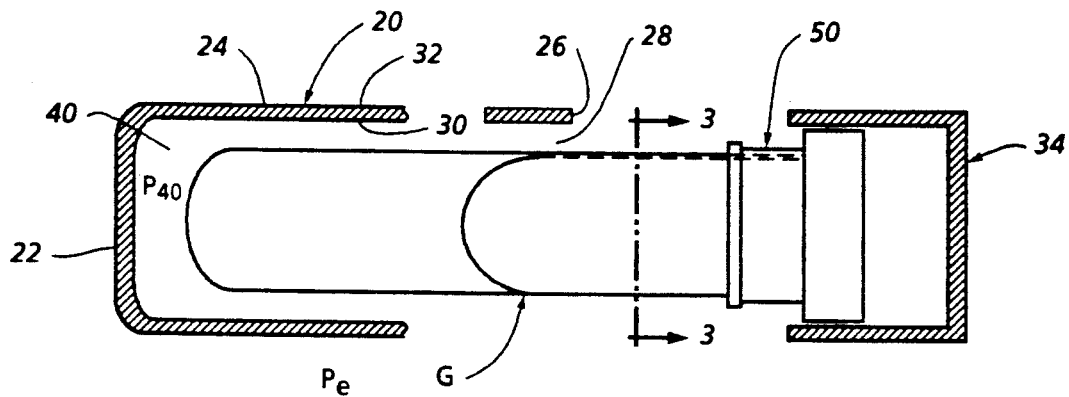
FIG. 2 is an exploded cut away side elevational view of the container and a protective garment.

Shown in FIG. 2 is an air-impermeable container 20 having an end wall 22 and a side wall 24 that terminates in a rim 26. The rim defines an opening 28 through which the protective garment G passes. Wall 24 includes an inner surface 30 and an outer surface 32, and a lid 34 sealingly closes the container. The container can be of any suitable shape, such as cylindrical or the like.

Figure 3:
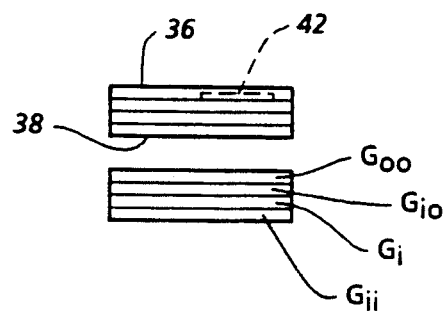
FIG. 3 is an elevational view taken along line 3—3 of FIG. 2.

As shown in FIG. 3, the garments are stored in the container in a layered condition with one garment, such as garment $G_i$ inside its next neighbor, garment $G_{io}$. This configuration defines an innermost garment $G_{ii}$ and an outermost garment $G_{oo}$. The outermost garment has an outer surface 36 that is located adjacent to the container wall inner surface 30 and the innermost garment has an inner surface 38 that is open to the atmosphere surrounding the container and into which the user places his or her appendage that is to be covered by the garment. The garments are stored in the container so that some portion of each garment, such as cuff portion 18 of a glove, is folded over rim 26 to be located outside container wall 24 with outside surface 36 adjacent to wall outer surface 32. The purpose of this folded over portion will be understood from the ensuing discussion.

As indicated in FIG. 2, a vacuum is placed on area 40 between the outermost garment and the inner surface of the container walls. As used herein, the term "vacuum" means a pressure $p_{40}$ less than pressure $p_e$ in the atmosphere surrounding the container. Pressure $p_e$ is generally equal to atmospheric pressure. Therefore $(p_{40} - p_e) < 0$, and this quantity will be referred to as a negative pressure. This negative pressure causes the garments to be forced towards the container wall when the innermost garment is exposed to atmospheric pressure. This causes the garments to "open up" to receive the user's body member as soon as the innermost garment inner surface is exposed to environmental pressure. In the case of a glove, the user merely slides his or her hand into the gloves and withdraws his or her hand with the glove thereon. A release layer 42 which can include powder, mylar or the like, can be interposed between adjacent garments to facilitate withdrawing one garment from another.

Figure 4:
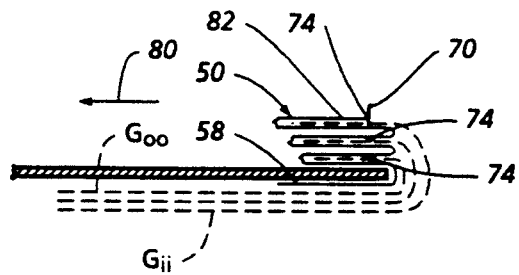
FIG. 4 is a partial end elevational view of one portion of a container in which protective garments and a sealing means are shown.
Figure 5:
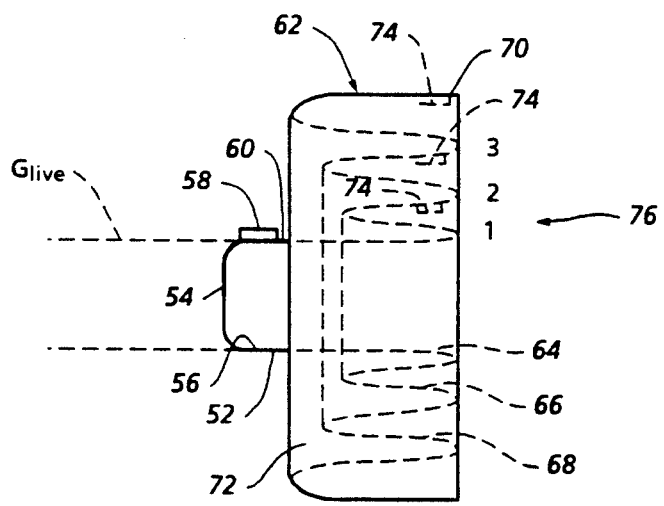
FIG. 5 is a side elevational view of a sealing means.
Figure 6:
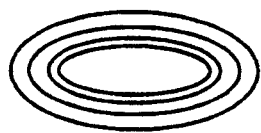
FIG. 6 is a top plan view of the FIG. 5 sealing means.

A sealing means 50 is used to prevent environmental pressure from degrading the vacuum in area 40. The sealing means is best shown in FIGS. 4-6, sealing means 50 includes a tubular body 52 having a first end 54 into which the garments fit with the outside surface of the outermost garment being adjacent to inner surface 56 of body 52. Adhesive 58 is located on outer surface 60 of body 52 adjacent to end 54 and secures the body to inner surface 30 of the container wall in an airtight manner. Adhesive 58 circumnavigates body 52, and is shown as a small area in FIG. 5 for the sake of convenience.

Sealing means 50 further includes an accordion folded section 62 on a second end thereof. The accordion folded section includes a plurality of folds 64, 66 and 68 with a free end 70 forming an outermost perimeter of section 62. End 70 can form a skirt 72 surrounding the folds as shown in FIG. 5, or it can be simply a string that hangs freely from the last fold. Each fold has adhesive 74 thereon. The adhesive areas are shown in FIG. 5 as small rectangular areas for the sake of convenience, but can surround the fold to form an annular ring of adhesive if suitable. The purpose and function of the adhesive will be understood from the ensuing discussion.

As is best shown in FIG. 4, each of the garments has its second end (such as end 16 of glove 10) interleaved between the folds of the accordion fold section. The adhesive 74 on each of the folds attaches the sealing means to the garment in an airtight but releasable manner. Therefore, there is an airtight, but releasable, seal formed between each garment and the sealing means and between the sealing means and the container wall. As each garment is removed from the container, the seal between that garment and the sealing means is broken; however, due to the nature of the accordion fold, the airtight seal between the garments and the container is not broken and the vacuum remains applied to the outermost garment while environmental pressure remains applied to the inner surface of the innermost remaining garment thereby inflating that innermost garment.

The sealing means is pulled away or rolled down as indicated by arrow 80 in FIG. 4 as each garment is removed. Markings 82 on the sealing means successively become exposed as the sealing means is moved in direction 80. These markings include indicia of how many garments remain in the container whereby a user will be warned when it is time to replace the container.

An alternative form of the sealing means is shown in FIG. 7 at 50'. Sealing means 50' includes a free tab 70', with adjacent accordion folds 64', 66' and 68' being connected together, with ends 86 being located inside the container and being interleaved between the garments. A shoulder 88 is located on the container wall adjacent to the opening 28.

To reduce possible stress to the garments and therefore prolong the shelf life of the product, the container can have an air-tight cap or bag on it. Cap 34 shown in FIG. 2 can serve this purpose. In such a form, the pressure could be reduced inside the container (i.e., inside the innermost garment) to leave the garments in a "relaxed" state until they are ready for use. The "relaxed" state results because the inner and outer pressures are the same on the garments. When the container is initially opened, the seal between the cap and the container body will be broken, and ambient air press e will be applied to the innermost garment. All garments would then assume an "inflated" state since the pressure between the outermost garment and the container is much less than ambient.

The special container of the present invention can be dispensed from vending machines, or the like, as indicated in FIG. 8. As shown in FIG. 8, a container C is stored in a housing H for storage or shipping purposes.

As mentioned above, the container of the present invention can be used in conjunction with any protective garment, and a surgical glove was disclosed in FIG. 1. However, the garments can include condoms, and such a container is illustrated in FIGS. 9A-9D. The container C' is identical to the container discussed above and is flexible so it can be stored in a nearly planar configuration as indicated in FIG. 9A. The wall of the container is squeezed to force it open and into the open condition shown in FIG. 9D. Otherwise, the container operates and functions exactly as discussed above.

It is understood that while certain forms of the present invention have been illustrated and described herein, it is not to be limited to the specific forms or arrangements of parts described and shown.

I claim:

1. A protective garment container comprising:
   A) an airtight container having a wall with a rim defining an opening, said container having an internal pressure that is less than the pressure of the environment surrounding said container to define a negative pressure differential;
   B) a plurality of gloves located inside said container, said gloves including an outermost glove and at least one innermost glove inside said outermost glove, each glove having a cuff portion overlapping said rim, each glove further having an outer surface and an inner surface with said outermost glove outer surface being located adjacent to said container wall and being exposed to said container internal pressure, the inner surface of the innermost glove being exposed to environmental pressure when said innermost glove is being donned by a user whereby said negative pressure differential exists between said innermost glove inner surface and said outermost glove outer surface; and
   C) sealing means releasably attached to each glove and to said container wall and including a flexible airtight body having a first end attached to said container wall and a second end attached to said outermost glove and further including releasable and airtight attaching means mounted on said sealing means body and releasably and sealingly attaching said sealing means body to the cuff portion of each glove and forming an airtight seal between said container wall and said outermost glove.

2. The protective garment container defined in claim 1 wherein each glove is folded over said rim so that the cuff of each glove is located outside said container.

3. The protective garment container defined in claim 2 wherein said sealing means includes an accordion folded portion adjacent to said sealing means body second end with said gloves being interleaved in said sealing means accordion folded portion.

4. The protective garment container defined in claim 3 wherein said releasable attaching means are located on said sealing means body in said accordion folded portion.

5. The protective garment container defined in claim 4 wherein said sealing means body one end is attached to an inner surface of said container wall, and said sealing means body second end is attached to an outer surface of said outermost glove.

6. The protective garment container defined in claim 5 wherein said releasable attaching means attaches said sealing means to an outside surface of said innermost glove.

7. A condom container comprising:
   A) an airtight container having a wall with a rim defining an opening, said container having an internal pressure that is less than the pressure of the environment surrounding said container to define a negative pressure differential;
   B) a plurality of condoms located inside said container, said condoms including an outermost condom and at least one innermost condom inside said outermost condom, each condom having a cuff portion overlapping said rim, each condom further having an outer surface and an inner surface with said outermost condom outer surface being located adjacent to said container wall and being exposed to said container internal pressure, the inner surface of the innermost condom being exposed to environmental pressure when said innermost condom is being donned by a user whereby said negative pressure differential exists between said innermost condom inner surface and said outermost condom outer surface; and p1 C) sealing means releasably attached to each condom and to said container wall and including a flexible airtight body having a first end attached to said container wall and a second end attached to said outermost condom and further including releasable and airtight attaching means mounted on said sealing means body and releasably and sealingly attaching said sealing means body to the cuff portion of each condom and forming an airtight seal between said container wall and said outermost condom.

8. The condom container defined in claim 7 wherein each condom is folded over said rim so that the cuff of each condom is located outside said container.

9. The protective garment container defined in claim 8 wherein said sealing means includes an accordion folded portion adjacent to said sealing means body second end with said condoms being interleaved in said sealing means accordion folded portion.

10. The condom container defined in claim 9 wherein said releasable attaching means are located on said sealing means body in said accordion folded portion.

11. The protective garment container defined in claim 10 wherein said sealing means body one end is attached to an inner surface of said container wall, and said sealing means body second end is attached to an outer surface of said outermost condom.

12. The protective garment container defined in claim 11 wherein said releasable attaching means attaches said sealing means to an outside surface of said innermost condom.

13. A package containing at least two body part protective garments comprising:
A) an airtight container having a wall with a rim defining an opening, said container having an internal pressure that is less than the pressure of the environment surrounding said container to define a negative pressure differential;
B) a plurality of garments located inside said container, said garments including an outermost garment and at least one innermost garment inside said outermost garment, each garment having a cuff portion overlapping said rim, each garment further having an outer surface and an inner surface with said outermost garment outer surface being located adjacent to said container wall and being exposed to said container internal pressure, the inner surface of the innermost garment being exposed to environmental pressure when said innermost garment is being donned by a user whereby said negative pressure differential exists between said innermost garment inner surface and said outermost garment outer surface; and
C) sealing means releasably attached to each garment and to said container wall and including a flexible airtight body having a first end attached to said container wall and a second end attached to said outermost garment and further including releasable and airtight attaching means mounted on said sealing means body and releasably and sealingly attaching said sealing means body to the cuff portion of each garment and forming an airtight seal between said container wall and said outermost garment.

14. The package defined in claim 13 wherein each garment is folded over said rim so that the cuff of each garment is located outside said container.

15. The package container defined in claim 14 wherein said sealing means includes an accordion folded portion adjacent to said sealing means body second end with said garments being interleaved in said sealing means accordion folded portion.

16. The package container defined in claim 15 wherein said releasable attaching means are located on said sealing means body in said accordion folded portion.

17. The package container defined in claim 16 wherein said sealing means body one end is attached to an inner surface of said container wall, and said sealing means body second end is attached to an outer surface of said outermost garment.

18. The package container defined in claim 17 wherein said releasable attaching means attaches said sealing means to an outside surface of said innermost garment.

19. The protective garment container defined in claim 3 wherein each fold is of a different length with an outermost fold being the longest fold.

20. The protective garment container defined in claim 3 wherein said container further includes a cap sealingly attached to said wall adjacent to said rim.

* * * * *